United States Patent
Amir et al.

(12) 
(10) Patent No.: US 6,911,202 B2
(45) Date of Patent: Jun. 28, 2005

(54) COSMETIC REPAIR USING CARTILAGE PRODUCING CELLS AND MEDICAL IMPLANTS COATED THEREWITH

(76) Inventors: Abraham Amir, 2 Hashikma Street, 40 600 Tel Mond (IL); Reva Amir, 2 Hashikma Street, 40 600 Tel Mond (IL)

( * ) Notice: Subject to any disclaimer, the term of this patent is extended or adjusted under 35 U.S.C. 154(b) by 0 days.

(21) Appl. No.: 10/066,753

(22) Filed: Feb. 6, 2002

(65) Prior Publication Data

US 2002/0106352 A1 Aug. 8, 2002

Related U.S. Application Data

(60) Provisional application No. 60/266,442, filed on Feb. 6, 2001.

(51) Int. Cl.$^7$ ................................................ A61K 7/00
(52) U.S. Cl. ..................................... 424/93.7; 424/401
(58) Field of Search .................................. 424/93.7, 401

(56) References Cited

U.S. PATENT DOCUMENTS 4,469,676 A * 9/1984 Hecmati

OTHER PUBLICATIONS

Atala et al. (J. Urol. (1993),vol. 150, pp. 745–747).*
Brittberg et al. (NEJM (1994), vol. 331, pp. 889–895).*
Merriam–Webster's Collegiate Dictionary, 10$^{th}$ edition, 1997, p. 1187.*
Park et al. (Facial Plastic Surgery (1995), vol. 11, No. 4, pp. 278–283).*
Kim et al. (Plastic and Reconstructive Surgery (1994), vol. 94, No. 2, pp. 233–237).*
Repair of Rabbit Articular Surfaces with Allograft Chondrocytes Embedded in Collagen Gel, Wakitani et al., The Journal of Bone and Joint Surgery, vol. 71–B, No. 1., Jan. 1989, pp. 74–80.
Autologous Cultured Fibroblasts as Cellular Therapy in Plastic Surgery, Boss et al., Clinics in Plastic Surgery, vol. 27, No. 4, Oct. 2000, pp. 613–626.
Long–Term Follow–Up of the Fate of Xenogeneic Transplants of Chondrocytes Implanted into Joint Surfaces, Robinson et al., Transplantation, vol. 52, No. 2, pp. 380 382, 1991.
Autologous Chondrocyte Transplantation for Reconstruction of Isolated Joint Defects: the Assaf Harofeh Experience, Robinson et al., IMAJ, vol. 2., Apr. 2000, pp. 290–295.
Advanced Techniques in Autologous Chondrocyte Transplantation, Minas et al., Complex Topics in Knee Surgery, vol. 18, No. 1, Jan. 1999, pp. 13–44.
Repair of Large Full–Thickness Articular Cartilage Defects with Allograft Articular Chondrocytes Embedded in a Collage Gel, Wakitani, et al., Tissue Engineering, 1998 vol. 4, No. 4, pp. 429–444.

* cited by examiner

*Primary Examiner*—Susan D. Coe
(74) *Attorney, Agent, or Firm*—Heslin Rothenberg Farley & Mesiti P.C.

(57) ABSTRACT

A method of cosmetically repairing a skin contour irregularity in a subject is provided. The method is effected by introducing cartilage producing cells into the skin contour irregularity thereby effecting cosmetic repair thereof. A medical implant coated with cartilage producing cells is further disclosed.

7 Claims, 2 Drawing Sheets

COSMETIC REPAIR USING CARTILAGE PRODUCING CELLS AND MEDICAL IMPLANTS COATED THEREWITH

This application claims the benefit of Provisional Application No. 60/266,422, filed Feb. 6, 2001.

FIELD AND BACKGROUND OF THE INVENTION

The present invention relates to methods of using cartilage producing cells, such as chondrocytes, for repairing cosmetic defects such as skin contour irregularities. The present invention further relates to implantable medical devices coated with chondrocytes and, more particularly to coating of implants (natural and artificial) with chondrocytes and or and/or their progenitors as a means of reducing unfavorable host response to the implant.

Cosmetic Repair

Plastic surgeons, dermatologists and their patients continually search for new and approved methods for treating damaged or aging skin. Historically, the treatment of facial wrinkles was primarily accomplished with the use of chemical peels or dermabrasion. The use of chemical peels has fallen out of favor, because it is difficult to accurately control and predict the depth of tissue injury after such peels are applied. Deeper chemical peels in particular have an increased risk of hypopigmentation and scarring.

Soft tissue fillers, such as collagen, have also been used for treatment of skin imperfections. These fillers are typically injected subcutaneously in a manner which enables filling and thus smoothing out skin contour irregularities such as wrinkles and scars.

Use of collagen as a dermal filler has several inherent disadvantages. These disadvantages typically include dissolution within 3 months, localized hypersensitivity in 1–6% of subjects, hypopigmentation, induration and multiple nodules as a result of foreign body granulomas (Boss et al. (2000) Clinics in Plastic Surgery 27(4): 613–626).

Synthetic dermal fillers offer an alternative to collagen. However, commercially available fillers such as Artecoll™, silicone and hyaluronen™ have not been approved for use in the United States. Further, some subcutaneous fillers, such as AlloDerm™ and SoftForm™ require surgical insertion, and might result in infection, reabsorption, malposition and rejection (Boss et al. (2000) Clinics in Plastic Surgery 27(4): 613–626).

Medical Implants

Non-self implants are used in many fields of medicine, such as: plastic surgery, orthopedics, maxillo-facial surgery, etc. The main disadvantage of prior art implants is the physiologic response they provoke following implantation. This response, which is typically induced locally around such implants is the body's attempt to reject the implant, or to isolate it from the body by creating a capsule around it. While a capsule may isolate the implant from a systemic immune response, it can also contract and cause distortion and pain of the organ. For example, a breast prosthesis induces capsule formation around it. In a study by Melmed (Plast Reconstr Surgery (1998) 101(5): 1364–73) 66% of the implanted women had severe capsular-contracture (III or IV Baker Degree).

Several approaches for reducing the physiological response to an implant have been suggested in the prior art. For example, Nishibe et al. (J Cardiovasc Surg (Torino) 2001 42(5):667–73) describe bonding of fibronectin to high porosity expanded polytetrafluoroethylene grafts as a means of improving host acceptance of implants. Rinsch et al. (Transplantation 2000 Feb. 15;71(3):345–51) teach transient immunosuppression as a means of increasing host tolerance for encapsulated xenogenic cells implanted into a subject. Neither of these methods employs cells. As such, the effect must be transient.

There is thus a widely recognized need for, and it would be highly advantageous to have, methods of using chondrocytes to effect cosmetic repair and chondrocyte coated implants devoid of the above limitation.

SUMMARY OF THE INVENTION

According to one aspect of the present invention there is provided a method of cosmetically repairing a skin contour irregularity in a subject, the method including introducing cartilage producing cells into the skin contour irregularity thereby effecting cosmetic repair thereof.

According to another aspect of the present invention there is provided a medical implant implantable in a subject including non-biological implant material coated with cartilage producing cells, the cartilage producing cells being for reducing a physiological response to the implant in the subject.

According to further features in preferred embodiments of the invention described below, the method further includes harvesting and optionally culturing the cartilage producing cells prior to the introducing.

According to still further features in the described preferred embodiments the skin contour irregularity is selected from the group consisting of a rhytid, a subcutaneous defect and a depression. Depressions may be, for example, the result of scarring or previous injury.

According to still further features in the described preferred embodiments introducing is effected via subcutaneous injection.

According to still further features in the described preferred embodiments the physiological response is selected from the group consisting of an immune response, an inflammatory response, encapsulation, ossification, calcification and infection.

According to still further features in the described preferred embodiments the device includes an intermediate layer being for increasing adherence of the cartilage producing cells to the non-biological material.

According to still further features in the described preferred embodiments the intermediate layer includes fibronectin, silicone or a combination thereof.

According to still further features in the described preferred embodiments the cartilage producing cells are selected from the group consisting of chondrocytes and chondrocyte progenitor cells.

According to still further features in the described preferred embodiments the cartilage producing cells are harvested from the subject.

According to still further features in the described preferred embodiments cartilage producing cells are harvested from a source syngeneic with respect to the subject.

According to still further features in the described preferred embodiments the cartilage producing cells are harvested from a source allogeneic with respect to the subject.

The present invention successfully addresses the shortcomings of the presently known configurations by providing methods which utilize chondrocytes to effect cosmetic repair and implantable medical devices coated with an immunoprotective layer of chondrocytes.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
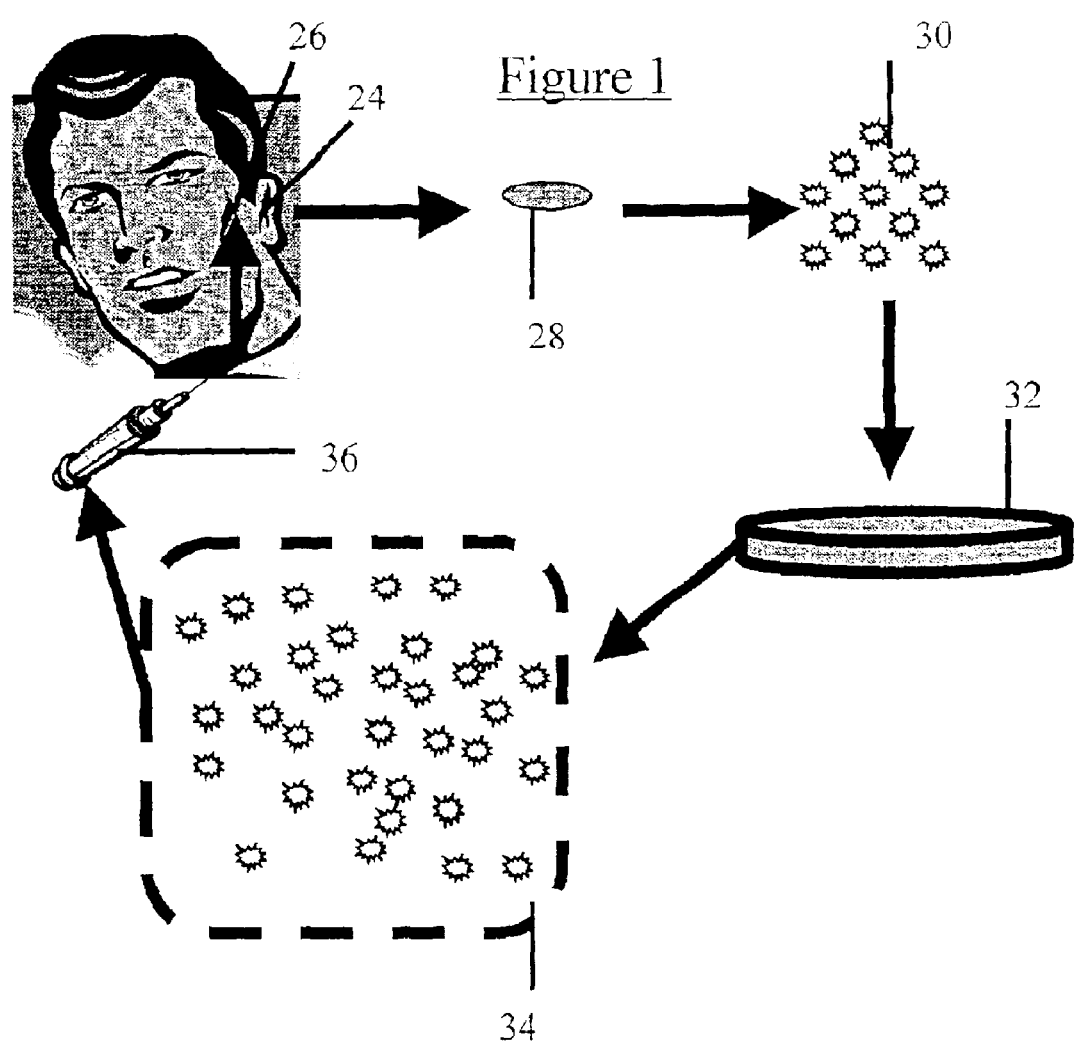
FIG. 1 schematically illustrates the steps employed by the method of cosmetically repairing skin contour irregularities of the present invention.

The present invention is of methods for using chondrocytes to effect cosmetic repair of skin contour irregularities. Specifically, the present invention can be used to repair cutaneous contour irregularities in a minimally invasive fashion.

The present invention is further of implants coated with chondrocytes or their progenitors as a means of reducing unfavorable host response to the implant. Specifically implants according to the present invention are resistant to encapsulation and inflammatory response.

The principles and operation of methods and implants according to the present invention may be better understood with reference to the drawings and accompanying descriptions.

Before explaining at least one embodiment of the invention in detail, it is to be understood that the invention is not limited in its application to the details of construction and the arrangement of the components set forth in the following description and pictured in the drawings. The invention is capable of other embodiments or of being practiced or carried out in various ways. Also, it is to be understood that the phraseology and terminology employed herein is for the purpose of description and should not be regarded as limiting.

While the use of chondrocytes in the art is well known, such use has typically been limited to reconstructive surgery and tissue repair.

Park and Ward (Facial Plast Surg (1995) 11(4): 278–83) teach tissue-engineered cartilage for implantation and grafting. Their teachings are directed to culture of chondrocytes on a three-dimensional biodegradable template which is first briefly incubated in vitro, then implanted into a recipient host. The template then resorbs and is replaced with new cartilage produced by the chondrocytes. Use of a template prevents injection of cultured chondrocytes and requires invasive implantation techniques that make these teachings ill suited to cosmetic repair of cutaneous contour irregularities such as wrinkles and scars.

Kim et al (Plast Reconstr Surg (1994) 94(2): 233–40) teach cartilage engineered in predetermined shapes employing cell transplantation on synthetic biodegradable polymers. These teachings are similar to those of Park and Ward and are ill suited to cosmetic repair of cutaneous contour irregularities for the same reasons.

Sims et al. (Plast Reconstr Surg 1996 98(5): 843–50) teach injectable cartilage using polyethylene oxide polymer substrates. Sims et al. specifically teach use of polyethylene oxide polymer substrates and teaches against use of chondrocytes in cosmetic applications. Specifically, Sims et al concluded that control specimens from eight implantation sites consisting of chondrocytes alone or polyethylene oxide substrates did not demonstrate any gross or histologic evidence of neo-cartilage formation.

U.S. Pat. No. 5,944,754 also to Vacanti teaches tissue re-surfacing with hydrogel-cell compositions and methods for generating new tissue on a surface, e.g., a surface of damaged or lost tissue of a structure or organ in a mammal. The methods involve applying a thin layer of a liquid hydrogel-cell composition to the surface; and allowing the liquid hydrogel-cell composition to solidify, thereby forming a matrix that enables the tissue precursor cells to grow and generate new tissue. The surface can be internal, e.g., the surface of an organ or the internal surface of a blood vessel, or external, e.g., skin. These teachings require matrix formation and dispersal of cells therein. Use of a matrix is a disadvantage with respect to cosmetic repair of contour irregularities.

U.S. Pat. No. 5,902,741 to Purchio et al. teaches three-dimensional cartilage cultures. Specifically, Purchio teaches a method of stimulating the proliferation and appropriate cell maturation of cells and tissues in three-dimensional cultures in vitro using TGF-.beta. Teachings of Purchio are limited to in-vitro culture. Further, teachings of Purchio et al. require use of TGF beta and the use of a three dimensional substrate which would require an invasive procedure to implant. In summary, the teachings of Purchio et al. can not be used for cosmetic repair of skin contour irregularities.

U.S. Pat. No. 6,139,578 to Lee et al. teaches preparation of cell seeded ceramic compositions, specifically a synthetic, poorly crystalline apatitic (PCA) calcium phosphate material seeded with cells. The compositions taught by Lee et al. are useful for a variety of applications, including in vivo and in vitro tissue growth (preferably bone or cartilage), osseous augmentation, and methods of diagnosing disease states by assaying tissue-forming potential of cells isolated from a host. The invention disclosed by Lee et al. also provides in vitro cell culture systems and cell encapsulation matrices. As with the patents cited hereinabove, Lee teaches use of a matrix, rendering his teachings ill suited for cosmetic repair of contour irregularities.

Brown et al. describe chondrocyte-smooth muscle cell compositions suitable for reconstructive applications. Brown et al note that the plastic properties of chondrocytes are sub-optimal for reconstructive applications and as such suggest mixing in of other cell types with the chondrocyte culture [e.g. chondrocytes plus smooth muscle cells; Brown et al. in Tissue Eng (2000) 6(4): 297–305].

Although numerous prior art publications teach various uses of chondrocytes in reconstructive surgery and tissue repair, none describe or suggest cosmetic repair of skin contour irregularities using chondrocytes or chondrocyte progenitors.

Thus, according to one aspect of the present invention there is provided a method of cosmetically repairing a skin contour irregularity in a subject. As used herein, the phrase "skin contour irregularity" refers to wrinkles of the skin, dermal depressions (rhytids), scars and the like.

The method according to this aspect of the present invention is effected by introducing cartilage producing cells such as chondrocytes or chondrocyte progenitors into the skin contour irregularity of the subject.

The present invention requires the use of cartilage producing cells, preferably chondrocytes, chondrocyte progenitor cells or mixtures thereof. In contrast to the prior art, cultures of these cartilage producing cells are preferably free of other cell types. As is described by Brown et al. the addition of other cell types (e.g., smooth muscle cells) can reduce the rigidity of a resultant mixed cell population, a quality which is disadvantageous in repair of skin contour irregularities which require a substantially rigid filler material.

The cartilage producing cells utilized by this aspect of the present invention can be obtained from a variety of tissue sources.

Preferably, cartilage is harvested with minimal functional harm and aesthetic damage. Preferably, harvest is from the auricle of the ear, most preferably from the concha such that a virtually invisible posterior scar remains. Alternately, harvest may be from, for example, the septum of the nose. In a case where the subject is undergoing surgery, and cartilage is being harvested for post surgical scar repair, other sources of cartilage may present themselves during surgery.

Typically, a piece of about 1×1 cm of the conchal cartilage is harvested and chondrocytes released therefrom are either used directly or cultured for a predetermined time period prior to administration (for further detail see the Examples section which follows).

Preferably, the cartilage is harvested from the subject to be treated and thus constitute an autologous graft. Alternatively, the cartilage producing cells are harvested from a source syngeneic with respect to the subject.

Since chondrocytes and the cartilage produced therefrom display weak immunogenicity, cells harvested from an allogeneic or even xenogeneic tissue source can also used.

Allografts and xenografts offer tremendous advantage with respect to autologous transplant. Use of allograft or xenograft cultures, if properly engineered to be immunologically neutral, allows maintenance of a small number of cell cultures for virtually all recipient subjects. This reduces patient trauma from tissue harvest, reduces the expense of generating primary cultures and reduces the waiting time required for a procedure.

Introducing chondrocytes or chondrocyte progenitors into a skin irregularity of the subject is carried out in a minimally invasive fashion, most preferably by injection of the cartilage producing cells subcutaneously. A small volume of cell suspension injected into the site of the subcutaneous contour defect will eventually fill the defect. Contact inhibition will prevent overfilling of the defect so that depressions do not become bumps. Chondrocytes harvested as described herein, and in particular autologous chondrocytes, can also be used as an immunoprotective layer for non-biological implants.

Thus, this aspect of the present invention provides novel and simple methodology for repairing skin contour irregularities. This methodology traverses the limitations of prior art methods by providing a filler material (chondrocytes) which can be easily produced and introduced into the subject's skin, does not elicit a physiological response (e.g., immune response) and is not absorbed over time. In addition, the cartilage formed from this filler material is more capable of resisting facial muscles movements than prior art fillers and as such, substantially reduce the chances of the wrinkles or rhytids returning.

Use of chondrocytes as an immunoprotective layer for tissue implants is known in the art (U.S. Pat. No. 5,741,685 to Vacanti). However, Vacanti does not teach or suggest coating of non-biological material with chondrocytes.

Thus, according to another aspect of the present invention there is provided a medical implant implantable in a subject. The medical implant is composed of non-biological implant material which is coated with cartilage producing cells, such as chondrocytes. For purposes of this specification and the accompanying claims, the phrase "non-biological" refers to any material which does not contain living cells.

The cartilage producing cells function to reduce a physiological response to the implant in the subject. The physiological response may be, for example, an immune response, an inflammatory response, encapsulation, ossification, calcification or infection.

To reduce such a physiological response, the cartilage producing cells utilized by this aspect of the present invention are preferably derived from the subject or a tissue source which is syngeneic with respect to the subject. It will be appreciated however, that other tissue sources (allogeneic, xenogeneic) may also be used, provided measures are taken to substantially reduce the immunogenicity of cartilage producing cells harvested from such sources.

In order to facilitate increased adherence of the cartilage producing cells to the device, an intermediate layer applied to the device may be employed. While many materials may be useful in construction of this intermediate layer will be known to those of ordinary skill in the art, fibronectin, silicone and combinations thereof have been found to be especially well suited for use in the context of the claimed device.

Thus, this aspect of the present invention provides a medical implant which does not elicit a physiological response following implantation, thus traversing problems associated with rejection of implants and as such prolonging the service life of such an implant within the subject's body.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include cellular and biochemical techniques. Such techniques are thoroughly explained in the literature. See, for example, "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); "Animal Cell Culture" Freshney, R. I., ed. (1986); and "Methods in Enzymology" Vol. 1–317, Academic Press; all of which are incorporated by reference as if fully set forth herein. Other general references are provided throughout this document. The procedures therein are believed to be well known in the art and are provided for the convenience of the reader. All the information contained therein is incorporated herein by reference.

As mentioned hereinabove, the method of cosmetic repair and the coated implants of the present invention both utilize cartilage producing cells.

The following Examples describe methodology which can be used for harvesting, culturing and utilizing such cells for cosmetic repair and implant coating.

Example 1

Harvesting Cartilage from a Donor

A cartilage explant of about 1×1 cm. is removed from an incision of approximately 1 cm in length along the posterior side of the concha of the auricle. A number 15 scalpel blade is well suited to this purpose, although other cutting implements may be employed without significantly changing the outcome of the harvest. The incision is then closed with resorbable suture material. The resultant scar is small and hidden by virtue of its location.

As is further described below, cartilage producing cells enzymatically released from the explant (further described below) can be used directly in cosmetic repair or coating of implants, or alternatively, such cells can be cultured prior to use.

Example 2

Culture of Cartilage Producing Cells

Several methods can be used for harvesting chondrocytes from the cartilage explant and for culturing harvested cells (see for example, Robinson et. al. Autologous chondrocytes transplantation for reconstruction of isolated joint defects: the Assaf Harofeh Experience. *Israel Medical Association Journal*, Vol. 2:290–295).

The following describes a method suitable for chondrocyte harvesting and culturing. The cartilage explant is digested with collagenase (0.2% weight/volume) in complete media containing 10% fetal bovine serum, 2 mM L-glutamine, non-essential amino acids, 50 mg/ml proline, 1 mM sodium pyruvate and 35 µg/ml gentamicin for 20 hrs at 37° C. Liberated cells (chondrocytes, chondrocyte progenitors) are spun, resuspended in complete medium, counted and plated at $10^6$ cells per T-150 flask. Cells can be passed at confluence (every 5–7 days) until sufficient cell number are achieved for purposes described in examples 3 and 4.

It is important that the stromal mass be suspended or floated in the medium during the incubation period in order to maximize proliferative activity. In addition, the culture should be "fed" periodically to remove the spent media, depopulate released cells, and add fresh media. Preferably, proline, a non-essential amino acid and ascorbate are also included in chondrocyte cultures.

Example 3

Cosmetic Repair by Introduction of Cartilage Producing Cells

Chondrocytes produced as describe above are dissociated by brief trypsinization monitored by microscopy. When sufficient disruption of the monolayer has been achieved, cells are washed 2 times in media without fetal calf serum and resuspended in saline or any other physiologically acceptable buffer for injection.

In order to facilitate injection, a cell density of $10^6$ cells/ml is loaded into a syringe fitted with a needle suitable for subcutaneous injection. Because it is desirable to leave no sign of the injection, a narrow gauge needle is employed. Preferably a 25 gauge, more preferably a 30 gauge needle is used. In general, approximately 1–2 ml. are required for each cosmetic repair site (e.g. each wrinkle), although repair of large areas may require larger volumes. However, it is generally best to prepare twice this amount since the exact volume to be filled is difficult to calculate. Injection of the chondrocytes is subcutaneous at the site of the contour irregularity. Because the cells can grow and/or proliferate, care is exercised not to overfill the contour irregularity. It will be appreciated that since the metabolic demand of chondrocytes and the cartilage produced therefrom is low, the filler material is maintained in a viable state for long periods of time by diffusion of nutrients and gasses from the surrounding tissue.

FIG. 1 schematically exemplifies cosmetic repair according to the teachings of the present invention.

Cosmetic repair is effected as follows, in a first step, cartilage 28 is harvested from a human tissue such as an ear 24 as described hereinabove. Cells 30 are dispersed and cultured 32 as described hereinabove.

Cells 34 from culture 32 are then loaded into syringe 36 and subcutaneously injected into the skin contour irregularity 26 (e.g., wrinkle scar, depression etc.) thereby effecting cosmetic repair thereof.

Example 4

Coating of a Medical Implant with Cartilage Producing Cells

Figure 2:
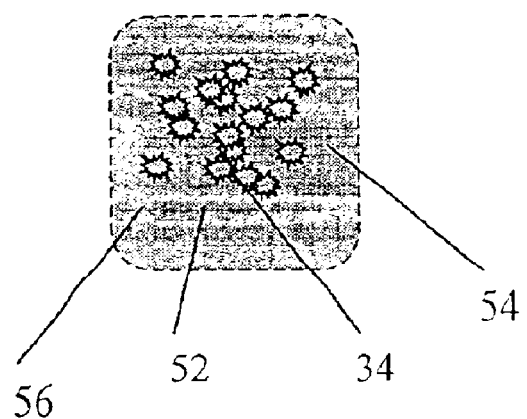
FIG. 2 is a schematic representation of a medical implant coated with an immunoprotective layer of chondrocytes fabricated according to the teachings of the present invention.

FIG. 2 illustrates a medical implant according to the teachings of the present invention. The medical implant of the present invention is fabricated by incubating non-biological implant material 52 (e.g., breast implant) in a solution containing 5 µg/ml of fibronectin overnight. Following incubation, the fibronectin solution is removed and replaced with chondrocytes 34 predissociated by brief trypsinization monitored by microscopy. An initial inoculum of $10^6$ cells/cm$^2$ of surface area of the implant material is employed. This allows confluent coverage of the device in 14 days. An additional 21 days of incubation are carried out in order to allow collagen 54 deposition by the newly formed chondrocytes. Optionally, non-biological implant material 52 is covered with an intermediate layer 56 which facilitates adherence of chondrocytes 34.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A method of cosmetically repairing a skin contour irregularity in a subject, the method comprising introducing a support free suspension of cultured isolated cartilage-producing cells devoid of solid particles into the skin contour irregularity thereby effecting cosmetic repair thereof.

2. The method of claim 1, wherein said cartilage producing cells are selected from the group consisting of chondrocytes and chondrocyte progenitor cells.

3. The method of claim 1, wherein said cartilage producing cells are harvested from the subject.

4. The method of claim 1, wherein said cartilage producing cells are harvested from a source syngeneic with respect to the subject.

5. The method of claim 1, wherein said cartilage producing cells are harvested from a source allogeneic with respect to the subject.

6. The method of claim 1, wherein the skin contour irregularity is selected from the group consisting of a rhytid, a subcutaneous defect and a depression.

7. The method of claim 1, wherein said introducing is effected via subcutaneous injection.

* * * * *